United States Patent [19]

Colonna

[11] Patent Number: 5,197,953
[45] Date of Patent: Mar. 30, 1993

[54] CAP ASSEMBLY

[76] Inventor: John Colonna, 1183 Coquille St., Sarasota, Fla. 34242

[21] Appl. No.: 727,013

[22] Filed: Jul. 8, 1991

[51] Int. Cl.⁵ ............................................. A61M 5/00
[52] U.S. Cl. ................................. 604/110; 604/263; 604/198
[58] Field of Search ............... 604/198, 263, 187, 192, 604/110

[56] References Cited

U.S. PATENT DOCUMENTS

| | | | |
|---|---|---|---|
| 2,876,770 | 3/1959 | White . | |
| 4,695,274 | 9/1987 | Fox | 604/263 X |
| 4,804,372 | 2/1989 | Laico et al. . | |
| 4,874,382 | 10/1989 | Lindemann . | |
| 4,892,521 | 1/1990 | Laico et al. . | |
| 4,894,055 | 1/1990 | Sudnak . | |
| 4,897,083 | 1/1990 | Martell . | |
| 4,911,693 | 3/1990 | Paris | 604/192 |
| 4,923,447 | 5/1990 | Morgan | 604/263 X |
| 4,927,416 | 5/1990 | Tomkiel | 604/198 |
| 4,998,924 | 3/1991 | Ranford | 604/198 |
| 5,011,479 | 4/1991 | Le et al. | 604/198 |
| 5,019,051 | 5/1991 | Hake | 604/198 |

Primary Examiner—John D. Yasko
Attorney, Agent, or Firm—Dykema Gossett

[57] ABSTRACT

The present invention relates to a protective device for use on a needle, for example hypodermic syringe. More particularly, the present invention is a capping assembly which can be used to cap or shield a needle immediately after it has been used. The capping assembly includes a generally tubular mounting member which has a tapered bore so that it can be easily slid upon, for example the barrel of a hypodermic syringe, but is difficult to remove due to the taper. Slideably mounted upon the mounting member is a sheathing member which is adapted to be slid down the mounting member to cover the needle after use. A locking member is provided between the sheathing member and the mounting member. In the preferred embodiment, the locking member included at least one protrusion extending outwardly from the mounting member and a capturing member extending inwardly from the sheathing member.

31 Claims, 2 Drawing Sheets

CAP ASSEMBLY

BACKGROUND OF THE INVENTION

The present invention relates to needles and more particularly to hypodermic syringes and the ability to easily cap the needle of the syringe after use.

It is becoming increasingly important for numerous reasons to be able to cover or cap needles, such as for example, hypodermic syringes, after they have been used. As is common, needles are initially capped prior to use to prevent injury to doctors, nurses, and others who come into contact with them. The needle is uncapped for use and then the syringe with needle attached is discarded. Many hospitals have now adopted the use of a specially designed canister distributed by Devon Industries, Inc. of Chatsworth, Calif. for holding the spent needles and syringes between the time they are inserted into the depository and then disposed of. This canister solely addresses the problem of disposal. It does not provide any protection for the user of a needle after the needle has been used, before it has been discarded, and also the hazards which may occur after it has been discarded, especially when improperly discarded.

A tremendous number of needles are used daily in hospitals. Nurses and doctors and other technicians handle these needles in their daily activities. Normally, they are carefully handled and properly discarded. However, due to carelessness at times and due to the emergencies which regularly confront medical personnel, proper handling is not always possible. In an emergency situation, an injection may be given and as the needle is passed to another person, it may be carelessly accepted or dropped due to the urgency of the situation and carelessly picked up with injury resulting. Also, the mere routine nature of many hospital activities may result in carelessness in the handling of syringes with injury occurring to the user. Of course, with health concerns as they are today, as for example with AIDS, one careless act could result in tragic consequences.

In addition to the use of needles by hospitals and medical offices, there is an enormous number of needles used in homes. For example, there are an estimated 14,000,000 diabetics. Unfortunately, needles used in the home are typically disposed of by putting them in the common garbage. As should be clearly apparent, unprotected needles in the common garbage pose immense risk to all that handle the garbage and to workers and others at landfills etc., where the garbage ultimately ends up.

Once needles are disposed of, there is still the possibility of further health risks. As graphically displayed by the news media, improper disposal of hospital waste has resulted in the deposit of that waste on beaches, etc. An open syringe lying on a beach or found in a landfill could result in tragic consequences.

A way of reducing, if not eliminating the hazards of puncture by a syringe after use is to cap the needle after use. However, a capper mechanism would have to be easy and very quick to use and not pose further potential for injury as it is being used.

BRIEF SUMMARY OF THE INVENTION

The present invention provides a solution to the problem of exposed needles. The present invention provides a capping assembly which can be quickly and easily used, is economical and is adaptable to any syringe or other medical device which has a needle attached. Briefly, the capping assembly of the present invention will be described in connection with its use upon a syringe having a needle attached thereto.

The capping assembly includes a protective cap or sheath means which can be pushed by hand along the barrel of a hypodermic syringe until it covers the needle and locks in place. In the locked position, the end of the protective cap extends beyond the point of the needle protecting against puncture after use. The sheath is very easy to use. After the injection has been given, the sheath is merely grasped with the fingers and pushed forward to cover the needle. Alternatively, the sheath can be grasped with the fingers and as the needle is pulled out of the patient, the sheath is maintained in place and the hypodermic syringe is pulled within the sheath to conceal the needle. In the preferred embodiment, the sheath is a tube made of clear plastic, such as for example, highly translucent polypropylene.

The sheath is mounted to the needle by a mounting member. In the preferred embodiment, this member is a tubular member with a tapered bore. The bore has a smaller diameter at the front end of the mounting member which increases in size to the opposite end. The size of the openings and the taper can be determined to coincide with the diameter and taper of the specific syringe to which the capping assembly is to be attached. As should be understood by those of ordinary skill in the art, all hypodermic syringes have some degree of taper due to method of molding, but each can be significantly different. This is an important feature of the present invention, by making the tapered inside diameter of the mounting member to fit upon a specific brand of hypodermic, it can be adapted without any change to the syringe body tooling. In this way, the syringe can be inserted into the mounting member and pushed until it seats, for example, against the finger flange of the syringe. Due to the taper of the inner bore, the mounting means cannot be easily pulled off of the syringe because of frictional contact between the mounting member and the barrel of the syringe.

The locking mechanism of the preferred embodiment includes at least one outward protrusion, preferably a protruding from the mounting member ring, and clamping or capturing means formed in the wall of the sheathing means. Preferably, these capturing means are stitches locking tang which are formed in the wall of the sheathing means. Each locking tang has two inwardly protruding fingers which engage the ring to lock the outer sheath in place. In operation, the forward finger is engaged by the ring and is forced upwardly by the ring until the ring engages the rearward finger. At this point, the forward finger drops down along the front face of the guide ring so that the guide ring is captured between the front and rear fingers. In this way, the sheath cannot be pulled backwards or pushed forward and is locked in place, sheathing the needle.

DETAILED DESCRIPTION OF A PREFERRED EMBODIMENT

Figure 1:
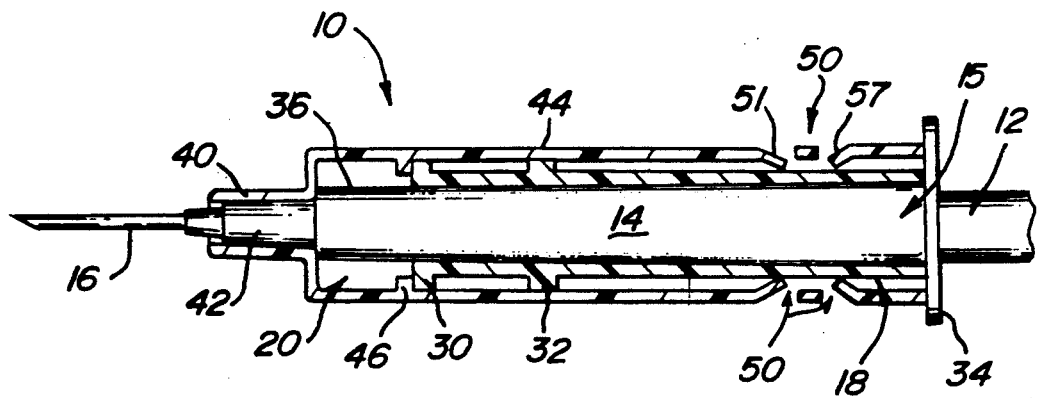
FIG. 1 is a sectional view of a hypodermic syringe with the capping assembly of the present invention mounted thereon in the unsheathed position.

With reference to FIG. 1, the cap assembly of the present invention as shown generally at 10. The illustrated cap assembly is mounted to a typical hypodermic syringe which is generally shown at 12. The hypodermic syringe 12 includes a barrel 14 which receives a typical plunger assembly shown generally at 15. A needle 16 is mounted at the forward end of barrel 14.

Figure 2:
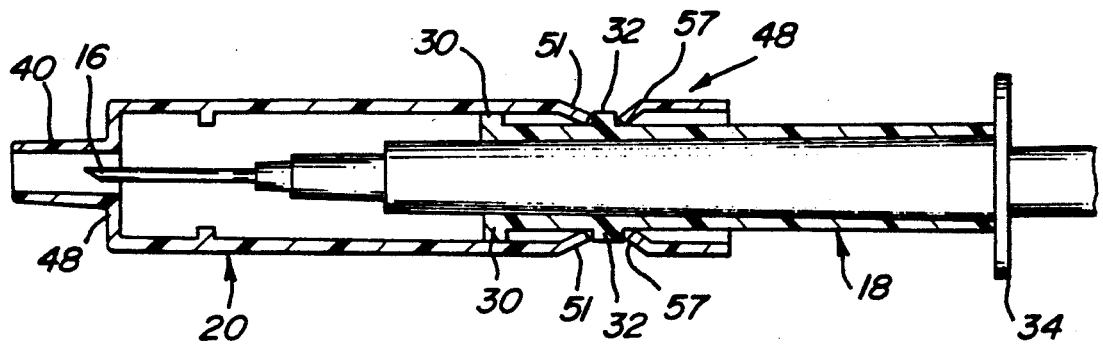
FIG. 2 is a sectional view of a hypodermic syringe with the capping assembly of the present invention mounted thereon in the sheathed position.

The cap assembly 10 of the present invention includes a mounting member 18 which is preferably made of a highly translucent polypropylene material. Member 18 is fitted over barrel 14 of syringe 12 and a protective cap member or sheathing member 20 which is slidably mounted upon mounting member 18. Sheathing member 20 is free to slide upon mounting member 18 so that it can be slid forwardly to sheath needle 16 after syringe 12 has been used. This can be seen in FIG. 2 and as shown in FIG. 2, the forward end of sheathing member 20 slides beyond the terminus of needle 16 to shield or conceal the needle 16.

Figure 3:
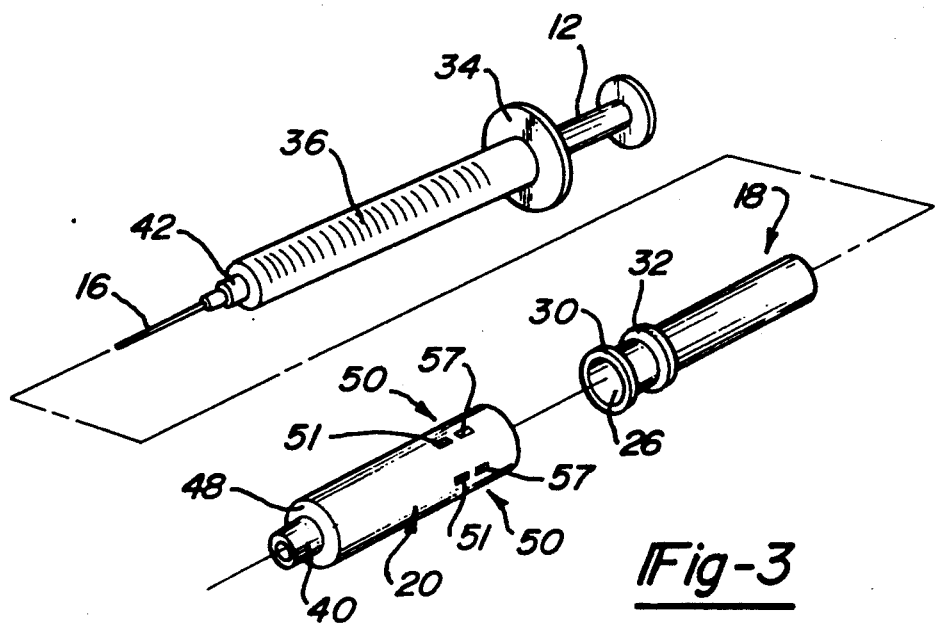
FIG. 3 is an exploded view of the capping assembly of the present invention and a hypodermic syringe on which it is mounted.
Figure 4:
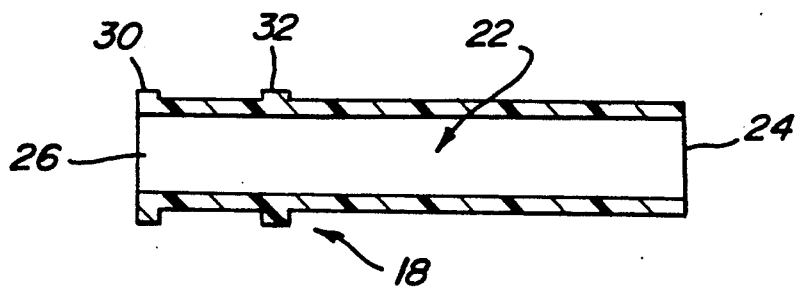
FIG. 4 is a cutaway view of the mounting member of the present invention illustrating the tapered inner bore.

With reference to FIGS. 1-4 and in particular FIG. 4, the mounting member 18 will be described in detail. In the preferred embodiment, mounting member 18 is a tubular member having a bore 22 which is tapered from a first smaller diameter at opening 26 to a larger opening 24 at the opposite end. As should be understood by those of ordinary skill in the art, the outer surface of all hypodermic syringes have some degree of taper due to the method of molding, but each can be different. An example of one taper is from a diameter of 0.250 inches at the end adjacent the needle to about 0.272 inches at the end just before the finger flanges. The taper of bore 22 would be substantially the same to ensure a tight fit. Due to the taper, the hypodermic syringe 12 can be inserted into the rear opening 24 of mounting member 18 with mounting member 18 being pushed onto syringe 12 until it engages the finger flange 34 of the syringe. The mounting member is relatively easy to push along the barrel 14 of syringe 12, but is very difficult to pull off the syringe 12. The tapered bore frictionally engages barrel 14.

Mounted upon the exterior or uniformly formed as part of mounting member 18 are protrusions 30 and 32. In the preferred embodiment, these protrusions take the form of rings which encircle the outer diameter of mounting member 18. The protrusions 30 and 32 act as stop members and locking rings respectively. They can also act as guides for contacting and guiding the sheathing member 20 as it is slid forwardly on syringe 12. As illustrated in FIG. 1, when the cap assembly 10 is initially mounted upon a syringe, protrusion 30 acts as a stop member and is engaged by a tab or ring 46 mounted to the interior of sheathing member 20. This defines the rearward most travel of sheathing member 20 with respect to the mounting member and the syringe. Protrusion or locking ring 32 forms one element of the locking mechanism which will be described in further detail below.

The sheathing member of the preferred embodiment is tubular and is preferably made of a highly translucent polypropylene material. It has a body portion 44 and a nose piece 40 which has a reduced diameter relative to the body portion 44. The reduced diameter nose piece 40 conforms to the locking tip 42 of the hypodermic syringe 12 as illustrated in FIG. 1. However, it should be appreciated, that the invention is not limited in any way to this configuration as the nose piece 40 is not necessary to proper functioning of the capping assembly, although it is preferred because of the reduced likelihood of contact with the needle when the nose piece is present. As shown in FIG. 2, the nose piece not only covers or shields the end of the needle, it provides a lesser diameter opening to reduce the likelihood of contact with the needle. If the nose piece were not of reduced diameter, there is a possibility that someone could insert a finger into a larger opening at the free end of the sheathing means and be punctured by the needle.

The body 44 of sheathing member 20 has an inside diameter which, in the preferred embodiment, is generally equal to the outside diameter of protrusions 30 and 32. In this way, the sheathing member 20 can slide upon the protrusions as it is slid along the barrel 14. Further, in the preferred embodiment, sheathing member 20 is tubular in configuration. However, it should be appreciated that other variations are possible. It may be desirable that the body of the sheathing member have a different geometric shape other than cylindrical, for example, it may be desirable to have sides with edges. Further, it may be desirable to have knurling along the outer body of sheathing member 20 for better gripping by the user or a finger flange at the forward end of member 20. Still further, the sheathing member 20 may not have a solid tubular shape as shown in the preferred embodiment, but may have split walls for reduced material, etc.

With reference to FIGS. 1-3, the locking mechanism shown generally at 48 in FIG. 2 will now be described. In the preferred embodiment, the sheathing member is formed with capturing means 50. As illustrated, the capturing means is in the form of locking tangs which are formed into the wall of sheathing member 20. The locking tangs have inwardly protruding fingers 51 which are adapted to capture protrusion 32 formed on mounting member 18. The forward most finger 51 is engaged by the rear surface of protrusion 32 and is forced upwardly out of the way so that protrusion 32 can pass by and engage the rear finger 53. Upon engagement, the forward finger 51 returns to its normal inwardly protruded position and is positioned in front of protrusion 32 capturing protrusion 32 between the fingers as illustrated in FIG. 2. In this position, the sheath is locked in place protecting against contact with the needle and cannot be moved rearwardly or forwardly.

As an added benefit, the capturing means 50 and the protrusion 32 could be made of two different color shades. Since it is preferred that they be made of a highly translucent polypropylene material, the capping assembly would have a band of color around the barrel of the syringe when the sheathing member 20 is shielding the needle. For example, the capturing means 50 could be yellow and the protrusion 32 could be blue. When the sheathing member 20 is locked in its second position, corresponding to the shielded position of the needle, there would be a band of green around the barrel of the syringe indicating visually that the needle has been properly shielded.

FIG. 1 is a cross-sectional view taken through a section extending through one of the locking tangs. As shown in FIG. 3, a circumferentially extending portion extends between locking tang fingers 51 and 57 and connects portions on each circumferential side of fingers 51 and 57. The portion seemingly floating in space in FIG. 1 between fingers 51 and 57 is this circumferentially extending portion which actually connects circumferentially spaced portions of sheathing member 20.

Figure 5:
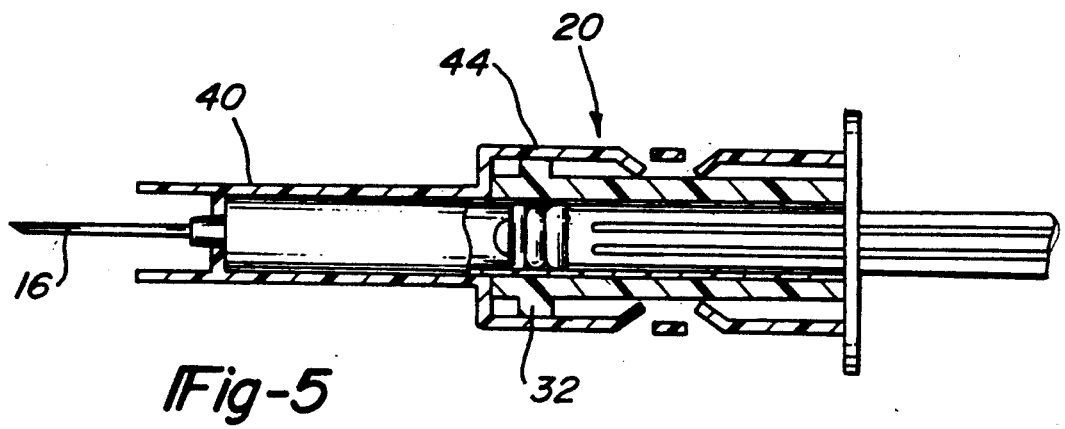
FIG. 5 is a further embodiment of the present invention mounted upon a hypodermic syringe.

With reference to FIG. 5, another embodiment of the present invention is shown. In this embodiment, the forward portion of the mounting member 18 has been removed and the nose piece 40 has been extended. As illustrated, nose piece 40 is positioned closely adjacent the barrel 14 of syringe 12 and if desired, barrel 14 could act as a guide means so that locking protrusions 32 would not have to engage the interior of sheathing member 20. This assembly works the same as that disclosed in FIGS. 1-4. In use, an injection is given and once the injection has been given, the body 44 of sheathing member 20 is grasped by the fingers of the user and either sheathing member 20 is pushed forwardly to shield needle 16 or syringe 12 is pulled rearwardly with sheathing member held in a fixed position with respect to the patient resulting in the needle 16 being concealed.

Figure 6:
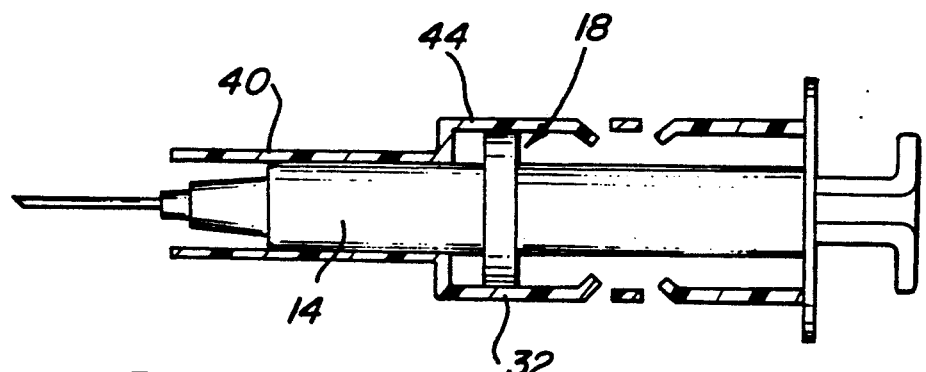
FIG. 6 is another embodiment of the present invention mounted upon a hypodermic syringe.

FIG. 6 is a further embodiment of the present invention where protrusion 32 is a single ring mounted to the barrel 14 of syringe 12. In all other respects, the assembly of FIG. 6 is the same as that of FIG. 5. It should be understood that the mounting member 18 could take various forms and shapes. It should be apparent to those of ordinary skill in the art that the locking protrusion 32 could be formed integrally with the barrel 14 of syringe 12 and does not have to be a separate piece. However, in order for versatility, having it as a separate unit makes the capping assembly 10 of the present invention more versatile for use on various sizes of syringes and other medical devices which employ needles.

Figure 7:
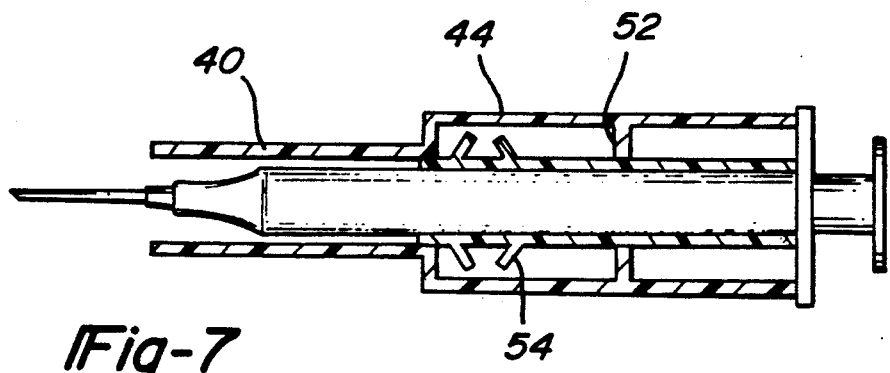
FIG. 7 is a still further embodiment of the present invention mounted upon a hypodermic syringe.

FIG. 7 is a still further embodiment of the present invention illustrating an alternative configuration of the locking protrusion and capturing means. In FIG. 7, the locking protrusion 52 extends outwardly from the inner wall of the body 44 of sheathing member 20. The capturing members, or locking tangs 54 extends outwardly from the outer wall of the mounting member 18. As illustrated, it should be appreciated by those of ordinary skill in the art that the elements of the locking member are interchangeable. Still further, other locking means could be used, the locking means illustrated being those which are preferred and considered most economical.

As should be apparent to those of ordinary skill in the art, the capping assembly of the present invention can be made by first molding the mounting member and then moulding the sheathing member. With reference to FIG. 3, the mounting member would be molded with the rings and the tapered bore. Once the individual pieces are molded, the mounting member would be inserted into the sheathing member with the stitching added after the mounting member is inserted. The completed assembly could then be mounted upon a syringe and sold as a unit or the assembly could be sold separately for mounting on the syringe by the syringe manufacturer or by the user of the syringe. As will be appreciated by those of ordinary skill in this art, other methods of making the capping assembly are available and the present invention is not intended to be limited by this disclosed method.

Other variations of this invention will also be appreciated by those of ordinary skill in the art. For example, although the sheath is preferably cylindrical, with a solid wall, the sheath could have split sidewalls to reduce material cost. Additionally, the protrusion 32 is shown as a ring, but those of ordinary skill will appreciate that it could take the form of a single or plurality of tabs extending outwardly from the mounting member or sheath. Further, the length of the capping assembly could be shortened with the assembly being positioned closer to the needle. These and other modifications and variations will become apparent to those of ordinary skill in this art.

It will be apparent to those skilled in the art that the foregoing disclosure is exemplary in nature rather than limiting, with the invention being limited only by the appended claims:

What is claimed is:

1. A capping assembly for a needle, said assembly comprising:
   a first member adapted to be mounted to said needle;
   a second member slidably mounted to said first member such that it can be moved axially with respect to said first member, said second member being adapted to slide along said first member to shield said needle;
   locking means for interlocking said first member and said second member at a predetermined relative position;
   said locking means including a projection on one of said first or second members said projection is a ring extending outwardly from said one of said first or second members; and a capturing means mounted on the other of said first or second members for capturing said projection after said second member has moved a predetermined distance;
   said capturing means is at least one locking tang formed in the wall of said one of said first or second members.

2. The capping assembly of claim 1, wherein said first member is generally tubular with the bore thereof being tapered from a first diameter at one end to a smaller second diameter at the opposite end;
   said opposite end being positioned nearest said needle;
   said syringe being inserted into said one end of said first member with said first member being pushed along said needle until it is properly seated, said smaller diameter of said opposite end preventing said first member from sliding off said needle.

3. The capping assembly of claim 1, wherein said second member has a first position wherein said needle is exposed and a second position wherein said needle is unexposed.

4. The capping assembly of claim 1, wherein said projection is a ring extending outwardly from said first member.

5. The capping assembly of claim 1, wherein said capturing means is at least one locking tang formed in the wall of said second member.

6. The capping assembly of claim 1, wherein said projection is a ring extending outwardly from said second member.

7. The capping assembly of claim 1, wherein said capturing means is at least one locking tang formed in the wall of said first member.

8. The capping assembly of claim 1, wherein said second member includes a nose portion that has a reduced diameter such that said needle can be shielded.

9. The capping assembly of claim 1, further including visual indication means for visually indicating that the second member is guarding the needle.

10. The capping assembly of claim 1, further including visual indication means for visually indicating that the second member is guarding the needle.

11. A cap assembly for shielding the terminus of a needle of a hypodermic syringe said syringe having a band, a plunger within said band and a needle affixed to the forward end of said barrel, said cap assembly comprising;
  mounting means for mounting said cap assembly to said hypodermic syringe, said mounting means being generally tubular with the bore thereof being tapered from a first diameter at one end to a smaller second diameter at the opposite end, said mounting means being adapted to grip said barrel such that said syringe can be inserted into said one end of said mounting means and said mounting means can be pushed along said barrel until it is properly seated along said barrel;
  sheathing means for sliding over said needle, said sheathing means being tubular and slidably mounted about the exterior of said mounting means;
  locking means for locking said sheathing means after it has been slid over said needle, said locking means including a projection on one of said mounting means or said sheathing means and mounted on the other of said mounting or sheathing means is a capturing means for capturing said projection after said sheathing means has moved a predetermined distance, said capturing means including at least one locking tang formed in the wall of said one of said mounting or sheathing means;
  whereby said syringe can be used for injections and after use, said sheathing means can be slid over said needle and locked to shield said needle.

12. The capping assembly of claim 11, wherein said sheathing means is generally tubular and is slidably mounted about said mounting means.

13. The capping assembly of claim 11, wherein said sheathing means has a first position wherein said needle is exposed and a second position wherein said needle is unexposed.

14. The capping assembly of claim 11, wherein said projection is a ring extending outwardly from said one of said mounting or shielding means.

15. The capping assembly of claim 11, wherein said projection is a ring extending outwardly from said mounting means.

16. The capping assembly of claim 11, wherein said capturing means is at least one locking tang formed in the wall of said shielding means.

17. The capping assembly of claim 11, wherein said projection is a ring extending outwardly from said sheathing means.

18. The capping assembly of claim 11, wherein said capturing means is at least one locking tang formed in the wall of said mounting means.

19. The capping assembly of claim 11, wherein said sheathing means includes a nose portion that has a reduced diameter such that said needle is shielded when said sheathing means is in said second position.

20. An improved syringe, said syringe having a barrel to which is attached a needle for injections, said improved syringe comprising;
  a guide means for guiding a protective cap, said guide means being adapted to be mounted to the barrel of said syringe, said guide means being generally tubular with the bore thereof being tapered from a first diameter at one end to a smaller second diameter at the opposite end, said opposite end being positioned nearest said needle, said guide means being adapted to grip said barrel such that said syringe can be inserted into said one end of said guide means and said guide means can be pushed along said barrel until it is properly seated;
  a generally tubular protective cap slidably mounted upon the exterior of said guide means such that it can be moved axially with respect to said guide means, said protective cap being adapted to slide along said guide means and extend beyond the terminus of said needle;
  locking means for interlocking said guide means and said protective cap at a predetermined relative position of said protective cap with said guide means, said locking means including a projection on one of said guide means or said protective cap and mounted on the other of said guide means or protective cap is a capturing means for capturing said projection after said protective cap has moved a predetermined distance, said projection is a ring extending outwardly from said one of said guide means or said protective cap and said capturing means is at least one locking tang formed in the wall of said one of said guide means or said protective cap.

21. The improved syringe of claim 20, wherein said guide means is generally tubular with the bore thereof being tapered from a first diameter at one end to a smaller second diameter at the opposite end;
  said opposite end being positioned nearest said needle;
  whereby said syringe can be inserted into said one end of said guide means and said guide means can be pushed along said syringe until it is properly seated, said smaller diameter of said opposite end preventing said guide means from sliding off said syringe.

22. The improved syringe of claim 20, wherein said protective cap has a first position wherein said needle is exposed and a second position wherein said needle is unexposed.

23. The improved syringe of claim 20, wherein said projection is a ring extending outwardly from said guide means.

24. The improved syringe of claim 20, wherein said capturing means is at least one locking tang formed in the wall of said protective cap.

25. The improved syringe of claim 20, wherein said projection is a ring extending outwardly from said protective cap.

26. The improved syringe of claim 20, wherein said capturing means is at least one locking tang formed in the wall of said guide means.

27. The improved syringe of claim 20, wherein said protective cap includes a nose portion that has a reduced diameter such that said needle is shielded when said protective cap is in said second position.

28. The capping assembly of claim 20, further including visual indication means for visually indicating that the second member is guarding the needle.

29. The capping assembly of claim 1, wherein said locking tang consists of a forward finger and a rear finger, said projection being received between said forward and rear fingers when said projection is captured.

30. The capping assembly of claim 11, wherein said locking tang consists of a forward finger and a rear finger, said projection being received between said forward and rear fingers when said projection is captured.

31. The improved syringe as recited in claim 20, wherein said locking tang consists of a forward finger and a rear finger, said projection being received between said forward and rear fingers when said projection is captured.

* * * * *